Feb. 16, 1954 H. C. SWIM Plant Pat. 1,254
ROSE PLANT
Filed Feb. 9, 1953
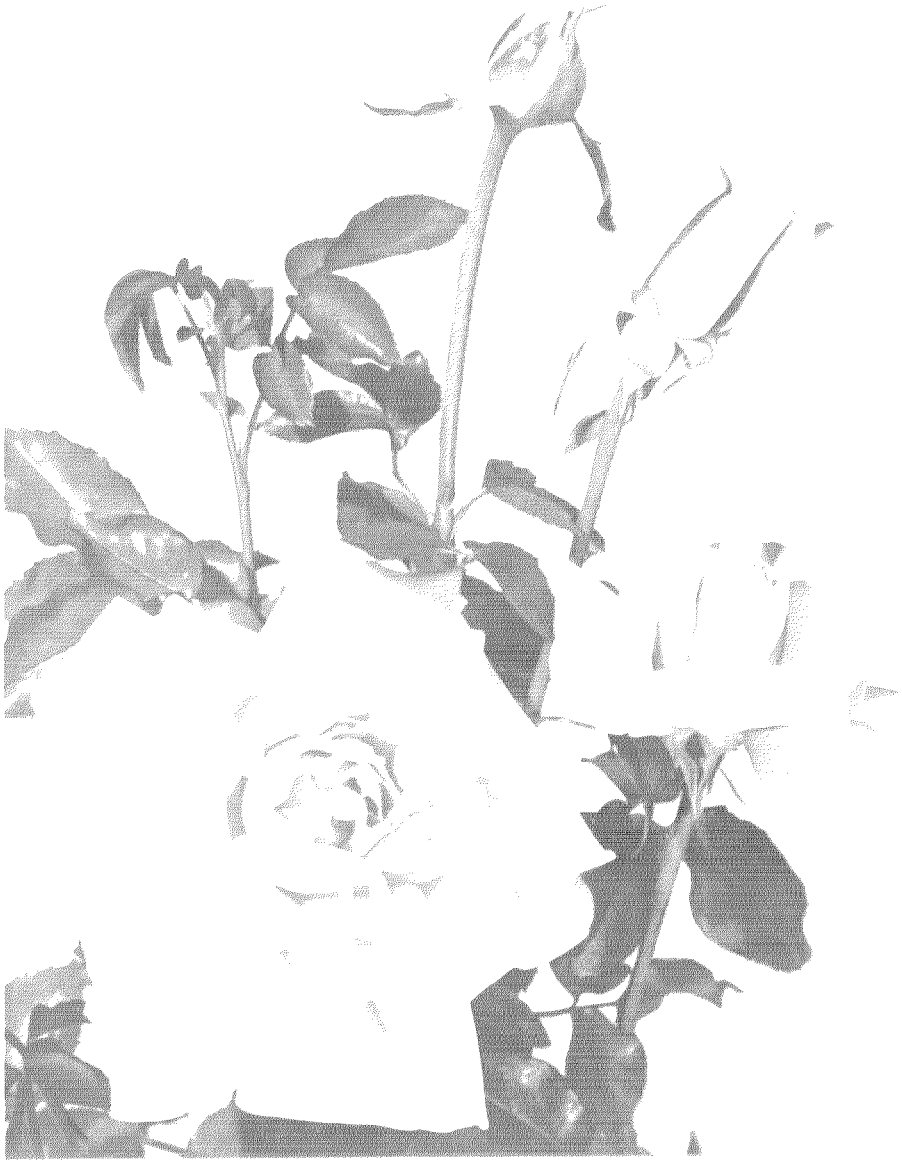
Inventor
H. C. Swim
By: Robb & Robb
Attorneys.

Patented Feb. 16, 1954 Plant Pat. 1,254

UNITED STATES PATENT OFFICE 1,254

ROSE PLANT

Herbert C. Swim, Ontario, Calif., assignor, by mesne assignments, to Stark Bro's Nurseries and Orchards Company, Louisiana, Mo., a corporation of Missouri Application February 9, 1953, Serial No. 336,028

1 Claim. (Cl. 47—61)

The present invention relates to a new and distinct variety of rose plant of the hybrid tea class, which was produced by me by crossing the variety "Charlotte Armstrong" (Plant Patent No. 455) with the variety "Signora Piero Puricelli," known as "Signora" in the United States (Plant Patent No. 201).

The primary objective in making this cross was to produce a new variety of rose plant which combines the best phenotypic characteristics of the two parent varieties, while at the same time emphasizing the recessive genes for yellow color present in both parents, but not expressed in them. This objective was fully achieved, as evidenced by the fact that my new variety is possessed of the following unique combination of outstanding characteristics which distinguish it from its parents, as well as from all other varieties of its class:

(1) The exceptional vigor of the plant as attributed to inheritance from both parents;

(2) The much-branched habit of growth of the plant, as is typical of the seed parent "Charlotte Armstrong," but with a more erect habit that is characteristic of the pollen parent "Signora";

(3) The very long, flowering stems which are characteristic of the pollen parent;

(4) The presence of very few prickles on the flowering stems and few prickles generally on the entire plant, which characteristics are typical of the pollen parent;

(5) The continuity of the bloom which is characteristic of "Charlotte Armstrong"; and (6) The glossy, large foliage that is characteristic of "Signora," but which is produced in even greater abundance than it is on plants of "Charlotte Armstrong."

In comparison with its seed parent "Charlotte Armstrong," my new variety is characterized by blooms of a light yellow general color tonality, whereas the blooms of "Charlotte Armstrong" are light red, or more popularly described as blood red to cerise; the foliage of the new variety is glossy, as distinguished from the dull or non-glossy foliage of "Charlotte Armstrong"; there are substantially fewer prickles on the plant of the new variety than are found on the plant of the seed parent; the blooms of my new variety have a strong fragrance, whereas the blooms of the seed parent have only a slight to moderate fragrance; the plant of the new variety is more upright in its habit of growth than the plant of this parent; and the flowers of the new variety have approximately twice as many petals as the flowers of the seed parent.

As compared with its pollen parent "Signora," the light yellow color of the blooms of the new variety is readily distinguished from the color of the blooms of "Signora" which usually range in various shades of orange and apricot; there are no small prickles found on the peduncle of the new variety, as are found on the peduncle of "Signora"; the new variety produces blooms more freely than does this pollen parent, and is even more vigorous; the foliage of the new variety is more abundant than the foliage of this parent; and the new variety has approximately twice as many petals per flower as the flowers of the pollen parent.

Asexual reproduction of my new variety by budding at Ontario, California, shows that the foregoing characteristics and distinctions come true to form and are established and transmitted through succeeding propagations.

The accompanying drawing shows typical specimens of the flowers, stems and foliage of my new variety in different stages of development.

The following is a detailed description of the new variety, with color terminology in accordance with Robert F. Wilson's Horticultural Colour Chart (hereinafter identified as "Wilson") and Ridgway's Color Standards and Nomenclature (hereinafter identified as "Ridgway"), except where general color terms of ordinary dictionary significance are obvious:

Type: Tall; bush; outdoor; seedling; for cut flowers and for garden decoration.

Class: Hybrid tea.

Breeding: Seedling.

*Seed parent.*—"Charlotte Armstrong."

*Pollen parent.*—"Signora."

Propagation: Holds its distinguishing characteristics through succeeding propagations by budding.

*Flower*

Locality where grown and observed: Ontario, California.

Flowers borne: Usually singly; on strong, long stems.

Quantity of bloom: Very free, outdoors.

Continuity: Nearly continuous during growing season.

Fragrance: Strong; spicy.

Bud:

*Peduncle.*—Average length; average caliper to heavy; erect; usually smooth; some gland-tipped cilia. Color—near Lettuce Green, Plate V (Ridgway), shaded somewhat with between Deep Corinthian Red, Plate XXVII (Ridgway) and Indian Red, Plate XXVII (Ridgway).

*Before calyx breaks.* — Size — medium. Form—medium length; ovoid; with foliaceous appendages; with some tomentum and some glandular bloom on the surface of the bud; sometimes with stout, much-cut, bristle-like foliaceous parts extending beyond the tip of the bud equal to ¼ or more of its length.

*As calyx breaks.* — Color—near Aureolin, Plate 3/2, page 3 (Wilson), marked with between Azalea Pink, Plate 618/2, page 74 (Wilson) and Carmine Rose, Plate 621/2, page 75 (Wilson).

*Sepals.*—Inner surface—with fine, woolly tomentum. Margins—margins of alternate sepals with woolly tomentum; others lined with stipitate glands.

*As first petal opens.*—Size—average to large. Form—medium length to long; ovoid. Color: outside—between Aureolin, Plate 3/3, page 3 (Wilson) and Lemon Yellow, Plate 4/3, page 4 (Wilson), shaded lightly around outer edge of petal with near Azalea Pink, Plate 618/2, page 74 (Wilson); inside — between Lemon Yellow, Plate 4/2, page 4 (Wilson) and Lemon Yellow, Plate 4/3, page 4 (Wilson), shaded somewhat around outer edge of petal with near Azalea Pink, Plate 618/2, page 74 (Wilson).

*Opening.*—Opens up well; is not retarded from opening by cold, hot, wet or dry weather.

Bloom:

*Size, when fully open.*—Large; 4 inches to 5¼ inches.

*Petalage.*—Very double; from 50 to 60 petals, plus 7 to 10 petaloids; arranged regularly.

*Form.*—High-centered at first; becoming open later; petals being at first flat-cupped, with lateral margins somewhat reflexed for ½ to ¾ of upper portion of petal, and with apex sometimes reflexed; becoming flat later at maturity, with lateral margins reflexed for ¾ of upper portion of petal, and also with apex sometimes somewhat reflexed.

Petals:

*Texture.*—Medium thickness; leathery; with inside somewhat velvety and outside slightly shiny to satiny.

*Shape.* — Outside — broadly obovate, with apex flat. Intermediate—obovate, with apex rounded to flat. Inside—obovate, with apex rounded.

This description of a newly opened flower was made from a rose grown outdoors in the month of May, at Ontario, California:

*Color.*—Outside petal: outside surface—near Aureolin, Plate 3/3, page 3 (Wilson), with small area at base of petal near attachment near Aureolin, Plate 3/1, page 3 (Wilson); inside surface—between Canary Yellow, Plate 2/3, page 2 (Wilson) and Aureolin, Plate 3/3, page 3 (Wilson), with small area at base of petal near attachment near Aureolin, Plate 3/1, page 3 (Wilson). Intermediate petal: outside surface—between Lemon Yellow, Plate 4/2, page 4 (Wilson) and Lemon Yellow, Plate 4/3, page 4 (Wilson), shaded slightly around margins with near Azalea Pink, Plate 618/3, page 74 (Wilson); inside surface—near Lemon Yellow, Plate 4/2, page 4 (Wilson), shaded slightly around margins with near Azalea Pink, Plate 618/3, page 74 (Wilson). Inner petal: outside surface—near Lemon Yellow, Plate 4/2, page 4 (Wilson), shaded slightly around margins with near Azalea Pink, Plate 618/3, page 74 (Wilson); inside surface—near Lemon Yellow, Plate 4/1, page 4 (Wilson), shaded slightly around margins with near Azalea Pink, Plate 618/3, page 74 (Wilson).

This description was made from a rose that was open for 3 days outdoors in the month of May, at Ontario, California:

*Color.*—Outside petal: outside surface—near Aureolin, Plate 3/3, page 3 (Wilson), shaded only slightly with near Carmine Rose, Plate 621/3, page 75 (Wilson); inside surface—between Canary Yellow, Plate 2/3, page 2 (Wilson) and Aureolin, Plate 3/3, page 3 (Wilson). Inside petal: outside surface—near Aureolin, Plate 3/3, page 3 (Wilson); inside surface—between Canary Yellow, Plate 2/3, page 2 (Wilson) and Aureolin, Plate 3/3, page 3 (Wilson).

*General color effect.*—Newly opened flower—between Lemon Yellow, Plate 4/3, page 4 (Wilson) and Buttercup Yellow, Plate 5/3, page 5 (Wilson), shaded somewhat around margins with near Azalea Pink, Plate 618/3, page 74 (Wilson). 3 days open—near Aureolin, Plate 3/3, page 3 (Wilson).

*Behavior.*—Drop off cleanly; not particularly affected by cold, hot, wet or dry weather.

*Flower longevity.*—On bush in garden—3 days in May. Cut roses grown outdoors kept at living-room temperatures—2 days in May.

*Reproductive organs*

Stamens: Average number to many; arranged regularly about pistils.

Filaments: Medium length; 5 to 8 mm. long; most with anthers. Color—between Poppy Red, Plate 16/1, page 16 (Wilson) and Mandarin Red, Plate 17/1, page 17 (Wilson).

Anthers: Medium size to large; all open approximately at once. Color—upper side—margin near Geranium Lake, Plate 20/1 page 20 (Wilson); remainder near Lemon Yellow, Plate 4/2, page 4 (Wilson). Under side—between Aureolin, Plate 3/2, page 3 (Wilson) and Lemon Yellow, Plate 4/2, page 4 (Wilson).

Pollen: Moderate to abundant. Color—near Aureolin, Plate 3/3, page 3 (Wilson).

Pistils: Many; approximately 150 in number.

Styles: Moderately uneven in length; average length; thin to average caliper; bunched; 7 to 13 mm. in length. Color—near Sap Green, Plate 62/3, page 62 (Wilson), with near Carmine, Plate 21/1, page 21 (Wilson) toward stigma.

Stigma: Color—between Canary Yellow, Plate 2/3, page 2 (Wilson) and Aureolin, Plate 3/3, page 3 (Wilson).

Ovaries: Some protruding from calyx.

Hips: Average length; ovoid to globular; smooth; walls thick and fleshy. Color (half mature)—between Cosse Green, Plate V (Ridgway) and Lettuce Green, Plate V (Ridgway).

Sepals: Permanent; medium length; recurved. Color: Inside—near Lettuce Green, Plate V (Ridgway), masked by white wholly tomentum; outside—between Cosse Green, Plate V (Ridgway) and Lettuce Green, Plate V (Ridgway).

Seeds: Average number; usually medium size; normally 16 to 23 in number.

*Plant*

Foliage:

*Leaves.*—Compound of usually 5 to 7 leaflets; abundant; large; moderately heavy; leathery; glossy.

*Leaflets.*—Shape—ovoid, with acute apex and round base. Margin—simply serrate.

*Color.*—Mature: upper surface— near Cress Green, Plate XXXI (Ridgway); under surface—near Courge Green, Plate XVII (Ridgway) and Biscay Green, Plate XVII (Ridgway). Young: upper surface—near Light Cress Green, Plate XXXI (Ridgway), shaded with near Indian Red, Plate XXVII (Ridgway); under surface—near Mineral Red, Plate XXVII (Ridgway).

*Rachis (the supporting stem of the compound leaf).*—Average size. Upper side—grooved; hairy; with some stipitate glands on edges. Under side—sparsely prickly; with few stipitate glands.

*Stipules.*—Medium length; narrow to medium width; with short to medium length points turning out at an angle of less than 45°.

*Disease.*—Better than average resistance to mildew, as compared with other varieties grown under comparable cultural conditions at Ontario, California.

Growth:

*Habit.*—Upright; much-branched.

*Growth.*—Very vigorous.

*Canes.*—Heavy.

*Main stems.*—Color—near Oil Green, Plate V (Ridgway). Large prickles—few; medium length; hooked slightly downward; with moderately long base. Color—between Avellaneous, Plate XL (Ridgway) and Wood Brown, Plate XL (Ridgway). Small prickles—none. Hairs—none.

*Branches.*—Color—near Oil Green, Plate V (Ridgway), to near Lettuce Green, Plate V (Ridgway). Large prickles—few; medium length; hooked slightly downward; with moderately long, narrow base. Color — between Pecan Brown, Plate XXVIII (Ridgway) and Rood's Brown, Plate XXVIII (Ridgway). Small prickles—none. Hairs—none.

*New shoots.*—Color—between Calliste Green, Plate VI (Ridgway) and Parrot Green, Plate VI (Ridgway), shaded with near Deep Livid Brown, Plate XXXIX (Ridgway) and near Dark Livid Brown, Plate XXXIX (Ridgway). Large prickles—few; meduim length; hooked slightly downward; with moderately long, narrow base. Color— between Dull Indian Purple, Plate XLIV (Ridgway) and Anthracene Purple, Plate XLIV (Ridgway). Small prickles—none. Hairs—none.

I claim:

A new and distinct variety of rose plant of the hybrid tea class, substantially as herein shown and described, characterized particularly as to novelty by its unique combination of the very vigorous, much-branched and erect habits of its growth, the very long, flowering stems and the presence of very few prickles thereon and few prickles generally on the entire plant, the continuity of its bloom, the abundance of its large, glossy foliage, and the distinctive color and very double petalage of its blooms.

HERBERT C. SWIM.

No references cited.